United States Patent [19]
Lichtenstein

[11] Patent Number: 5,100,383
[45] Date of Patent: Mar. 31, 1992

[54] CATHETERS PERMITTING CONTROLLED DIFFUSION

[76] Inventor: Meir Lichtenstein, 18/159 Curzon Street, North Melbourne, Victoria 3051, Australia

[21] Appl. No.: 559,389

[22] Filed: Jul. 24, 1990

Related U.S. Application Data

[63] Continuation of Ser. No. 156,920, filed as PCT/AU87/00131, Mar. 8, 1987, abandoned.

[30] Foreign Application Priority Data

May 8, 1986 [AU] Australia .................. PH5800

[51] Int. Cl.⁵ .................................. A61M 29/00
[52] U.S. Cl. ........................... 604/96; 604/158; 604/164; 604/269; 604/271; 600/16
[58] Field of Search ........... 604/29, 43, 96, 158, 604/164, 265, 266, 269, 271; 600/16

[56] References Cited

U.S. PATENT DOCUMENTS

| 3,173,418 | 3/1965 | Baran | 604/61 |
| 3,589,356 | 6/1971 | Silverman | 604/271 |
| 3,598,127 | 8/1971 | Wepsic | 604/265 |
| 3,699,956 | 9/1972 | Kitrilakis et al. | 128/348 |
| 3,965,909 | 6/1976 | Waddell et al. | 604/269 |
| 3,981,299 | 9/1976 | Murray | 604/43 |
| 4,002,170 | 1/1977 | Hansen et al. | 604/269 |
| 4,008,710 | 2/1977 | Chmiel | 600/16 |
| 4,186,745 | 2/1980 | Lewis et al. | 604/265 |
| 4,352,048 | 7/1983 | Lucas et al. | 604/53 |
| 4,526,175 | 7/1985 | Chin et al. | 604/271 |
| 4,536,179 | 8/1985 | Anderson et al. | 604/266 |
| 4,604,094 | 8/1986 | Shook | 604/271 |
| 4,623,329 | 11/1986 | Drobis et al. | 604/29 |

FOREIGN PATENT DOCUMENTS 0984441  1/1983  U.S.S.R. .................. 604/271

*Primary Examiner*—John D. Yasko
*Assistant Examiner*—Anthony Gutowski

[57] ABSTRACT

A non-thrombogenic surface is provided by forming a reservoir from which anticoagulant solution can permeate through a flexible wall (5, 6) of bio-compatible permeable material. Such reservoirs can be used in catheters one form of which includes a hollow-walled tube reservoir with outer wall (5) and inner wall (6). The reservoirs may also be used in cardiac assist devices comprising a bladder (56) with an outer permeable wall (54) and an inner impermeable wall (55), means to introduce anticoagulant solution into the reservoir defined between these walls, and means (60) for the controlled inflation and deflation of bladder (56).

7 Claims, 2 Drawing Sheets

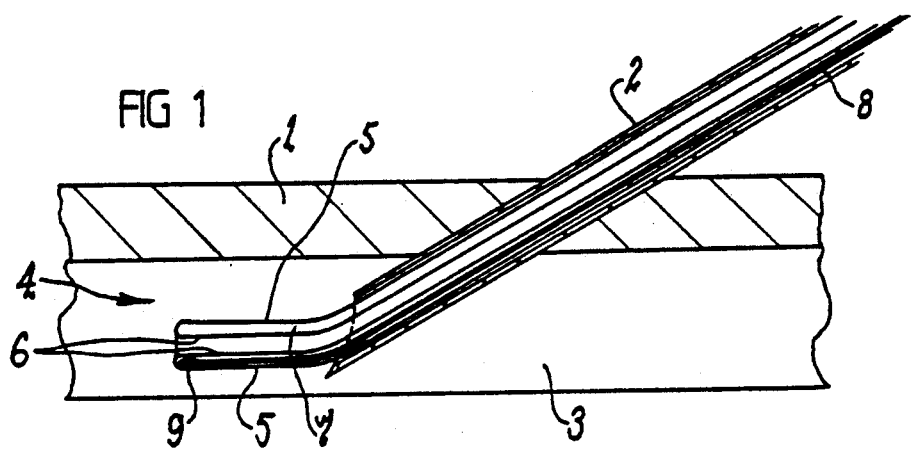
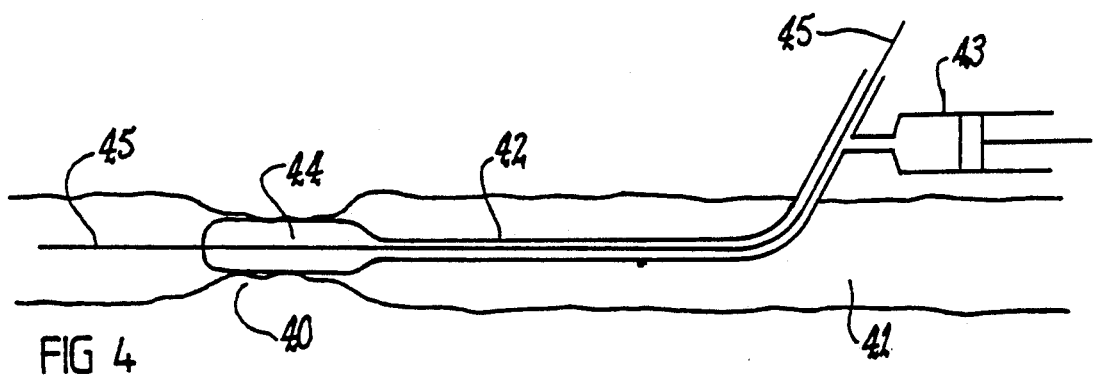
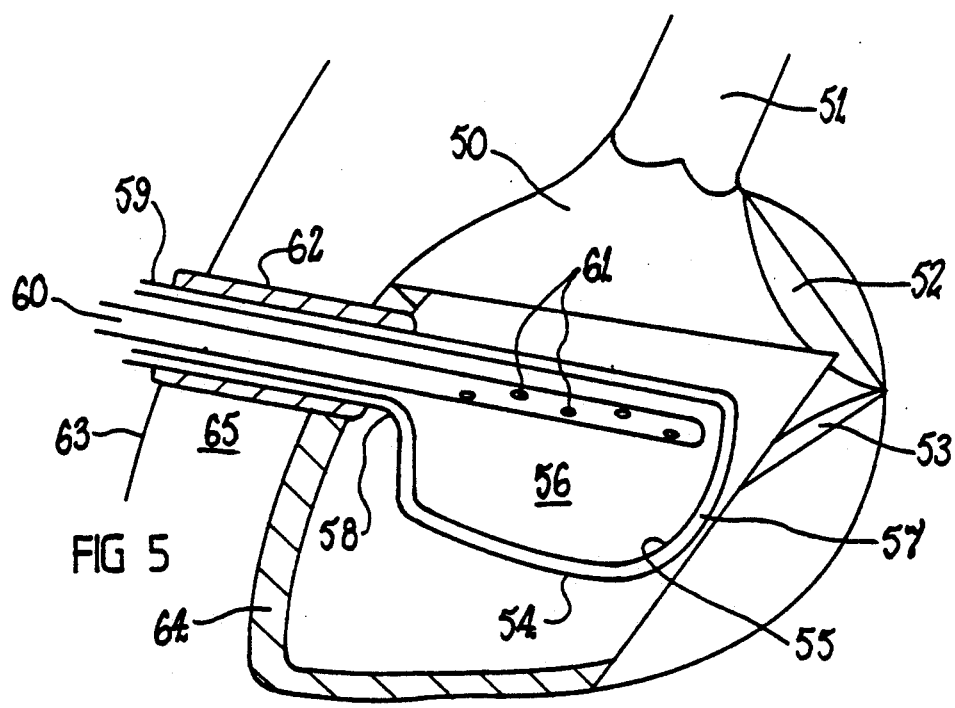

CATHETERS PERMITTING CONTROLLED DIFFUSION

This application is a continuation of application Ser. No. 07/156,920 filed as PCT/AU87/00131, Mar. 8, 1987, now abandoned.

BACKGROUND OF THE INVENTION

The invention relates to bio-compatible surfaces, in particular to non-thrombogenic surfaces, and is particularly concerned with the provision of vascular catheters and cardiac assist devices incorporating such non-thrombogenic surfaces.

That blood remains fluid in blood vessels is partly due to the fact that normal vascular endothelium does not promote blood coagulation. Foreign surfaces, both endogenous and exogenous, promote clotting in varying degrees. The degree of clotting appears to depend, inter alia, on the surface electrical charge and the property of wettability of the surface. The inactive coagulation factors, factor XII (Hageman factor) and factor XI, are activated by contact with foreign surfaces, and then the coagulation process is initiated. This process may be initiated in the intravascular space by such foreign surfaces as tumor cells, disrupted villi as in accidental antepartum hemorrhage, endothelial cells damaged by trauma and infarction, or by the introduction of foreign bodies such as catheters or the like.

Some silicone surfaces and a number of plastics materials have a weak effect in promoting blood clotting. However, even a weak thrombogenic effect makes such materials unacceptable for use in situations were clots which may be formed could block the flow of blood to vital organs such as the brain or heart. Non-thrombogenic properties are particularly desirable for intravascular prostheses, catheters and extracorporeal equipment such as heart-lung machines and the like.

Attempts have been made to impart non-thrombogenic properties by adding to, or otherwise modifying, the surface of various polymeric materials but such attempts have not been as successful as desired. In particular, such materials have not totally alleviated the problem associated with catheters and the like so that periodic replacement, for example during long term treatment, is necessary. Repeated replacement may cause extensive damage to blood vessels including partial or total collapse of the vessel or may cause scar tissue to form at the site of introduction thus making subsequent procedures more difficult.

BRIEF DESCRIPTION OF THE INVENTION

It is a principal object of the present invention to provide a bio-compatible surface which is non-thrombogenic for use in medical and related arts. It is another object of the invention to provide a catheter suitable for insertion into the venous or arterial system and comprised of such a surface. It is a further object of the invention to provide a cardiac assist device which is minimally invasive in its implantation and can be permanently placed for usage.

In accordance with the invention there is provided a reservoir having in use at least one bio-compatible non-thrombogenic surface, said reservoir being defined by flexible spaced-apart walls at least one of which is a bio-compatible polymeric material through which anticoagulant solution contained in use by said reservoir may permeate.

According to one preferred embodiment, the reservoir of the invention may be used in the formation of a catheter although it will be understood that the invention is not limited to this application. A catheter using the reservoir of the invention includes essentially a collapsible, flexible tube having a hollow wall consisting of an inner wall defining a central lumen and an outer wall separable from the inner wall so as to define a substantially annular interwall passageway. The inner and outer walls merge or are sealed at each end to fully enclose the interwall passageway thus forming the reservoir of the invention into which anticoagulant solution may be introduced.

The inner and outer walls of the catheter are sealed together at their distal ends or a hollow-walled tube in which the distal ends of the walls merge may be formed by turning one end of a single-walled tube back upon itself and drawing the end back over or through the tube until a hollow-walled tube half the length of the original tube is formed. The proximal ends of the tube walls may be separately connected to a common sealing member, or to coacting sealing members.

Tubing of this type may be formed from permeable bio-combatible polymeric material by conventional techniques such as extrusion, or fabrication from appropriate sheet stock.

The catheter may be introduced initially within the bore of a needle inserted into a vein or artery. (Unless otherwise indicated, reference herein to a vein is to be understood as including reference to an artery.) In this method of introduction, the hollow-walled tube reservoir of the invention also serves to allow a blunt-ended introducing device such as a flexible wire or rod to be passed into the annular space between the inner and outer walls of the catheter until the device reaches the distal end of the catheter. At this stage, the distal end of the catheter may still be within the needle but can then be pushed from the needle into the vein by advancing the introducing device. When the desired length of catheter has been pushed from the needle, anticoagulant solution can be introduced into the reservoir and the introducing device withdrawn. The distention of the catheter by the anticoagulant solution maintains the catheter in the vein after the needle has been withdrawn.

Although rolling catheters are known, they have found little general medical application prior to the present invention. A rolling catheter may be introduced into a vein via a conventional wide-bore hypodermic needle and syringe The present invention is applicable to the formation of rolling catheters where the required catheter diameter is large enough to avoid mechanical difficulties. In this application, use of hollow-walled tubing in accordance with the invention may assist the introduction of such catheters.

The rolling catheter may be introduced through the bore of an introducing needle or alternatively over the exterior of a needle or guidewire. The catheter may then be advanced within the vein by injecting anticoagulant solution at moderately high pressure into the interwall passageway of the catheter, thus inflating the catheter and forcing it to extend into the vein. To further extend the catheter after its initial inflation and extension, the pressure of the injected solution may be increased, thereby rolling the catheter out into the vein.

In use the central lumen of the catheter allows either aspiration of the blood or the introduction of conventional intravenous solutions.

In accordance with the present invention, catheters preferably include injection means so that anticoagulant solution may be injected into the interwall passageway of the catheter. The pressure of the anticoagulant solution in the interwall passageway of the catheter is maintained in use at least at, and preferably above, the pressure of the blood in the vein or other blood vessel in which the catheter is being used. The injection of anticoagulant solution may occur after the catheter has been placed in the desired position or the catheter may be advanced to the desired position under the hydrostatic pressure of the injected anticoagulant solution.

There may be provided reserve or additional catheter forming material, external to the point of entrance to the vein, for later further insinuation as considered appropriate by the user. Such reserve or additional material will preferably be integral with the catheter material within or around the introducing needle or guidewire and may be located within a reservoir or other container.

If necessary, the flexible walls of catheters using the present invention may be reinforced by the insertion of a stiffer material along part or all of the length of the catheter. For example, where a catheter is to be used for the aspiration of blood, the flexible walls may be reinforced by inserting a stiffer tube within the interwall passageway. The reinforcing tube may be withdrawn after aspiration has been completed and the catheter retained in the vein for intravenous infusion.

A further embodiment of the invention relates to the provision of a cardiac assist device. In this embodiment there is provided an inflatable bladder which may be percutaneously introduced into the recipient's heart. At the time of a cardiac arrest, the bladder may be introduced directly into the left ventricle percutaneously. Depending on the time available, the introduction may be performed under X-ray control. It is preferred that the bladder be introduced via a 14 or 12 gauge needle.

The bladder may comprise a sausage-like balloon, defined by an inner wall of flexible gas tight material, such as polyethylene. An outer wall of permeable biocompatible polymeric material spaced from the inner wall defines a reservoir in which the inner and outer walls merge with an integral hollow walled entry tube to the interior of the bladder. In accordance with the invention, anti-coagulant solution is introduced into the reservoir formed between the two walls to permeate through the outer wall of the implanted bladder and entry tube. Thus, the cardiac assist device will further include means to introduce anticoagulant solution into the reservoir.

The dual walled bladder may be introduced in toto as later described with reference to an accompanying drawing, or it may be formed in situ. Where the bladder is formed in situ a permeable membrane comprised of the bio-compatible polymeric material, impregnated with anticoagulant, is introduced by needle to form the outer wall of the bladder. A gas tight membrane comprised of, for example, polyethylene is then introduced such that it forms the inner wall of the bladder and is not in contact with blood circulating in the ventricular space. Means are also included as part of the cardiac assist device to enable the controlled inflation and deflation of the bladder.

For example, after anticoagulant solution is introduced into the so-formed reservoir, the needle used to introduce the inner wall is withdrawn and replaced by a stiff catheter of polyethylene or the like. This stiff catheter thus extends from within the implanted bladder to a position external to the patient's body. The end of the catheter within the bladder is open or may be provided with a plurality of holes along its length, through which carbon dioxide or other suitable gas may be admitted to, and removed from, the interior of the implanted bladder to thus alternately expand and contract the bladder. The admission and removal of the gas is preferably conducted by a low pressure pump connected to the distal end of the stiff catheter.

It is preferred that the volume of gas pumped in and out of the implanted bladder per second be slightly less than the volume defined by the bladder itself. Accordingly, for a bladder approximately 10 cm long and 4 cm in diameter, a pumping rate of 70 cc in and out/second for a patient at rest is preferred.

The inflation and deflation of the implanted bladder inside the left ventricle provides a propulsive force for the blood in the case of a severely failing heart. For cases of permanent heart failure it may be useful to insert two such devices into the left ventricle which could be used alternately, or to provide a back-up should one fail. A similar device could operate in the right ventricle if necessary. If desired, the bladder may be directed to lie inside the mitral valve as well as take over its functions, if necessary.

It is anticipated that the membranes comprising the bladder will require periodic replacement as some deterioration when used in vivo may be expected due to mechanical wear as well as protein and calcium deposition.

Among useful permeable bio-compatible polymeric materials which may be used to fabricate the permeable wall(s) of reservoirs according to the invention are Celanese CELGARD membrane, Tyvek polyethylene by Du Pont, expanded PTFE as used for arterial grafts, haemodialysis membrane material based upon cuprophane, polyhydroxy methyl methacrylate, haemodialysis membrane materials based on cellulose or acrylonitrile as produced by Rhone Poulenc, polycarbonate such as the polycarbonate dialysis membrane produced by Gambro, and polysulphonate or other dialysis membranes.

The thickness of the bio-compatible polymeric materials used will depend upon the particular application. However, permeable materials from 25 to 150 microns in thickness may be used with typical catheter materials being around 50 microns thick. Catheter materials do not need to be as thick as materials used for heart devices as they do not have to withstand the higher pressures applied in the heart devices. For heart devices, permeable materials of about 100 micron thick are typical. Where impermeable materials are used, thicknesses of 75 to 100 microns are typical and again, greater thickness materials are used for heart devices.

It is noted that prior art composite anti-thrombotic materials are typically not less then 1 mm thick and are stiffer (less flexible) than the materials used to make up the reservoirs of the present invention.

Conventional haemotological agents used as antithrombotics and/or anticoagulants may be used in forming the solutions used in this invention. Among these may be mentioned heparin (particularly low molecular weight heparin), disodium or dipotassium ethylenediamine tetraacetic acid (hereinafter referred to as EDTA), ammonium and potassium oxalate mixtures (hereinafter oxalate) and sodium citrate.

Calcium chelating agents, including lipid soluble agents such as diethyldithiocarbamate, ethylene diamine derivatives, penicillamine and hydroxy quinoline may also prove useful anticoagulants in the performance of the invention.

A further class of antithrombotic agents which may find application in the performance of this invention are the anti-platelet aggregation agents such as prostaglandin derivatives including PGE 1 and prostacyclin (including stable prostacyclin derivatives such as iloprost).

The anticoagulants may be formulated into physiologically acceptable concentrations with suitable conventional carriers. After injection into the interwall passageway, the anticoagulant solution may then diffuse through the permeable wall of the reservoir into the bloodstream thus reducing the tendency of clots to form on the reservoir surface.

Where high molecular weight heparin is used in the anticoagulant solution in a high concentration in order to assist the permeation of this anticoagulant, reservoirs fabricated from cuprophane as used in haemodialysis membranes are preferred. Such polymeric material is designed to transmit molecules of up to 15,000 daltons. Where low molecular weight heparins are used in the anticoagulant solution, the cellulose or acrylonitriles referred to above are preferred. From a haematological and biological point of view, the low molecular weight heparins are most preferred as bleeding at the site of a membrane/tissue interface is minimized.

If EDTA, oxalate or citrate anticoagulants are used, any of the above hydrophilic polymeric materials may be used.

Where lipophilic calcium chelators or prostaglandin derivatives are employed as the anticoagulant it is preferred that lipophilic polymeric membranes be used. Such membranes include polyethylene, polyethylene terephthalate (Mylar), polypropylene and polyvinyl chloride.

In order to avert or treat infection sited on the semipermeable membrane, there may be added to the anticoagulant solution conventional agents such as antibacterials, e.g. antiseptics or antibiotics, as considered appropriate. These can also diffuse out of the membrane to avert or treat infection in the surrounding tissue.

The prevention of infection is particularly desirable where a catheter enters and passes through the skin and tissue leading to the vein, or where a cardiac assist device passes through the skin and tissue leading to the heart. Accordingly a further feature of the invention is the provision of a collar of permeable material attached to the outer wall of the catheter or cardiac assist device and extending along said outer wall where the infection may arise in use. The collar defines, with the outer wall, an annular chamber into which an antibacterial or other suitable solution can be injected.

Continued bleeding from the site at which the skin has been broken and/or bleeding into the tissue between this site and the vein or other vessel may also be a problem which can, however, be readily overcome. If the pressure transmitted by the outer wall of the catheter or heart assist device is insufficient to stop the bleeding of the surrounding tissue, or if such bleeding is promoted by the outwardly permeating anticoagulant solution, the application of a surgical sealant to the site and/or to the relevant portion of the outer wall will generally stop the bleeding. Such sealants are currently available for spray dispensing.

In order to assist in the understanding of the invention, drawings of preferred embodiments are attached. The drawings are to be understood as showing example constructions only, so that their particularity is not to be understood as superceding the generality of the preceding description.

BRIEF DESCRIPTION OF THE DRAWINGS

FIG. 1 is a diagrammatic sectional view showing the insertion of a standard catheter tube incorporating a reservoir in accordance with this invention;

FIG. 4 diagrammatically shows a dilatation catheter according to a further embodiment of the invention.

FIG. 5 diagrammatically shows a left ventricular assist device according to a still further embodiment of the invention.

DESCRIPTION OF THE INVENTION

Figure 2:
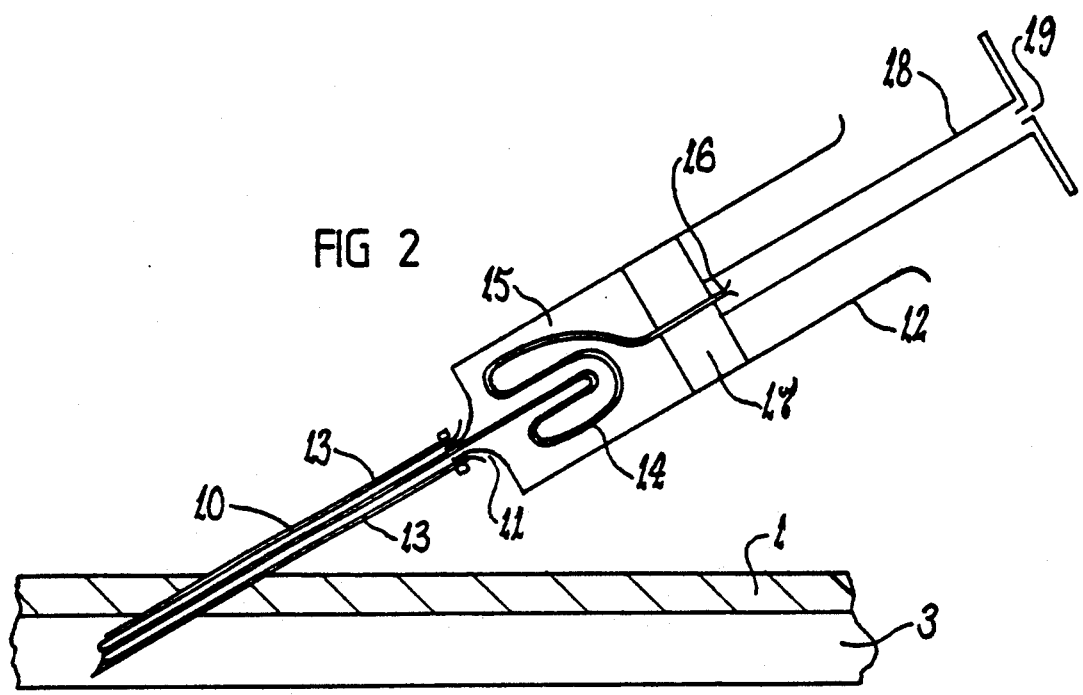
FIG. 2 diagrammatically shows the insertion of a rolling catheter according to one embodiment of the invention.

In FIG. 1, skin and associated tissue 1 is punctured by inserting a needle 2 and the tip of needle 2 is introduced into a vein 3. A tubular catheter 4 comprising an outer wall 5 and an inner wall 6 defining an interwall passageway 7 is initially within the needle 2. After the introduction of needle into the vein 3, an introducing device 8 having a blunt end 9 and lying within the interwall passageway 7 is used to push the catheter 4 into the vein 3. When the catheter has been inserted into the vein to the desired extent, the introducing device 8 is withdrawn. An anticoagulant solution is preferably injected to fill the interwall passageway 7 prior to insertion of the introducing device 8 and the pressure of the anticoagulant solution in passageway 7 is maintained after the 8 is withdrawn, so that anticoagulent solution can permeate through the biocompatible permeable walls 5 and 6.

In the embodiment shown in FIG. 2, the reservoir of the invention forms a hollow-walled tube of a rolling catheter. As illustrated, an introducing needle 10 is attached to the tip 11 of a syringe 12 with a free end portion of an outer wall 13 of the hollow-walled catheter wedged between the needle 10 and the tip 11. A reserve length 14 of catheter tubing comprising a permeable membrane in accordance with the invention is held in a barrel 15 of the syringe 12 with its free end 16 held by the cylinder 17 of a syringe plunger 18 which is hollow stemmed. Anticoagulant solution surrounds the reserve catheter tubing 14 in the barrel 15. The hollow stem of plunger 18 is connected at 19 for intravenous infusion or whatever other purpose may be intended for the catheter.

After the needle 10 has been inserted through the skin 1 into the vein 3, plunger 18 and the cylinder 17 are depressed thereby forcing anticoagulant solution from the barrel 15 into the hollow wall of the catheter within the needle 10. The pressure of the solution also forces the end of the catheter out of the needle 10 into the vein 3 and draws the reserve catheter tubing from the barrel 15 to form the extended length of catheter within the vein 3. When the desired length of catheter has been forced into the vein 3, the needle 10 may be withdrawn and appropriate protection placed over the catheter entry site.

Figure 3:
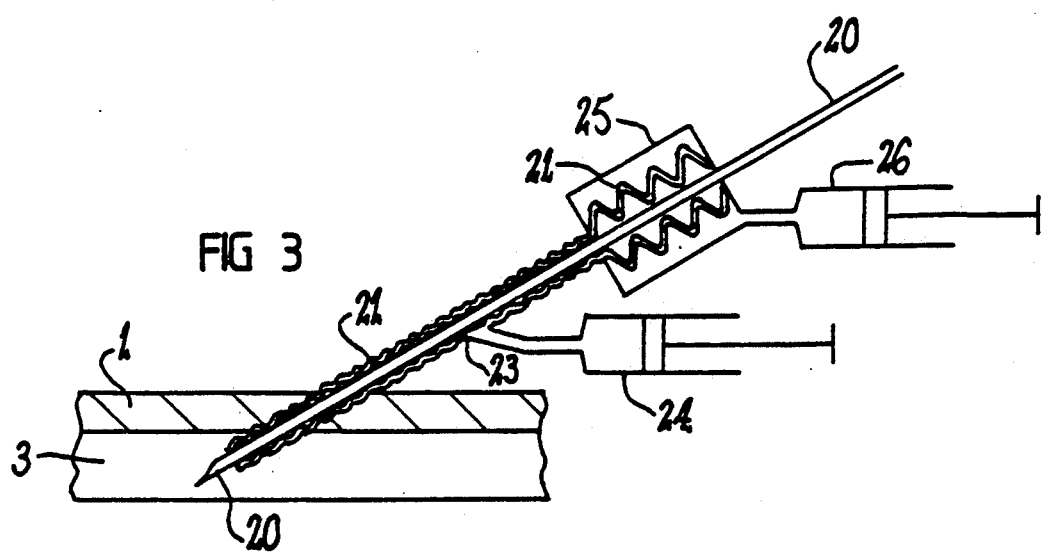
FIG. 3 diagrammatically shows an alternate means of insertion of a rolling catheter according to another embodiment of the invention.

FIG. 3 shows an alternative form of a rolling catheter incorporating the present invention. In this form, a fine gauge introducing needle or wire 20 is inserted along the bore of a hollow-walled catheter tubing 21 formed in accordance with the invention. The tubing 21 is compressed in somewhat corrugated form and lightly adhered to the needle 20. The outer wall of tubing 21 is shown as breached at 23 to allow connection of a syringe 24 containing anticoagulant solution so that the solution can be driven, when desired, into the interwall passageway of the catheter tubing 21. The location of breach 23 will, of course, allow all the tubing 21 to be used. A reserve length of catheter tubing 21 is held within a pressurized storage chamber 25. A syringe 26 may be used to maintain the pressure in chamber 25.

After the needle 20 is inserted through the skin and tissue 1 into the vein 3, anticoagulant solution is forced from the syringe 24 into the interwall passageway of tubing 21, in turn forcing the tubing 21 into the vein 3. When the desired length of tubing 21 has been forced into the vein 3, the pressure of solution in tubing 21 is maintained. Connection of the bore of tubing 21 to intravenous fluid supply or similar purpose is made at the junction of tubing 21 with chamber 25.

FIG. 4 illustrates a further alternative use of the reservoir of the present invention. In this figure the invention is shown as applied to the construction of a dilatation catheter.

The dilatation catheter diagrammatically illustrated is shown in position to dilate stenosis 40 formed in an artery 41. In this embodiment, the catheter 42 is of generally tubular form with its walls formed throughout of a permeable membrane allowing passage of anticoagulant solution forced into the lumen of the tube 42 from the syringe 43. The catheter tube 42 may be expanded at its inner end portion 44 by the anticoagulant solution which thus also serves to dilate this portion of the catheter.

A guide 45 extends through the lumen of tube 42 to assist insertion of the catheter and is preferably adhered to one side of the wall to prevent the tube from riding back over the guide as it is inserted. The guide 45 may itself be tubular in form to permit the continued flow of blood past the blockage of the artery caused when the catheter is dilated.

The cardiac assist device illustrated in FIG. 5 in the left ventricle of the heart is a further application of this invention. The diagrammatic drawing shows the left ventricular chamber 50 in part section, the aorta 51, mitral valve 52 and papillary muscle 53. The cardiac assist device includes an outer permeable membrane 54 surrounding inner gas- and liquid-impermeable membrane 55 which defines an inflatable bladder 56. The device 56 thus has an interwall passageway 57 into which anticoagulant solution may be introduced in accordance with the invention. Bladder 56 and outer membrane 54 are narrowed at a neck portion 58 to merge with an integral hollow-walled entry tube 59. (In FIG. 5 the diameter of entry tube 59 is exaggerated in relation to that of bladder 56 for greater clarity; the entry tube diameter is preferably as small as possible, for example 3-4 mm, while the diameter of the bladder when inflated may be approximately 4 cm.)

A feed tube 60 from a pump device (not shown) extends through the entry tube 59 into the bladder 56. Bladder 56 may be inflated by pumping a suitable gas through the feed tube 60 to exit holes 61. Feed tube 60 is also shown as provided with a collar 62. As described above, the collar 62 may be simply an impervious layer applied in the course of manufacture or during use of the device to prevent the anticoagulant solution from permeating through this part of the outer membrane 54. Alternatively or additionally, collar 62 may be formed to contain antibacterial solution which can diffuse outwards to prevent entry track infection For the desired percutaneous insertion of the cardiac assist device of FIG. 5, the bladder 56 is wound around the inner portion of the feed tube 60. The insertion of the device through the skin surface 63, heart wall 64 and intervening tissue 65 can then be made by passing the device through a needle of an appropriate internal diameter.

Laboratory tests conducted to date include the incubation of 2 ml of blood in pockets formed in double walled membranes in which anticoagulant solution was maintained in the interwall passageway. These severe static tests were performed at 20° C. using 10% citrate anticoagulant solution in double walled membranes formed from (a) polyacrylonitrile membrane approximately 25 microns thick (Rhone Poulenc),
(b) polycarbonate membrane approximately 25 microns thick (Gambro), and
(c) CELGARD membrane approximately 125 microns thick (Celanese).

Microscope examination of the blood after 45 minutes of static incubation revealed the formation in some cases of two or three platelet aggregates less than 25 microns in greatest dimension but no clotting. The formation of such platelet aggregates would not be clinically significant.

An in-vitro test in which a cardiac assist device of the kind described above was run for 160 hours to simulate the beating effect of an implanted device and did not lead to any deterioration of the device.

Catheters for intravenous infusion made in accordance with the invention have been successfully introduced into the veins of dogs. However the catheters were pulled out by the animals less then 16 hours after insertion so that the data on the antithrombogenic effect was not considered to be conclusive.

Catheters made and used according to the present invention provide several significant advantages over the prior art. Among these may be mentioned: 1. they are non-thrombogenic, 2. they are much softer than conventional catheters and as a consequence mechanical trauma to the blood and blood vessels is less likely to occur upon insertion or removal or while the catheter remains
3. they are better able to negotiate bends because the introducing force is not necessarily along the line of the catheter, but may be hydrostatic.

As previously mentioned, the catheter may be introduced via a conventional hypodermic needle or over a guide wire. This latter technique is particularly useful where arterial dilation is required. In this application the catheter would also be designed to dilate at the correct arterial site. An arteriotomy wherein such a catheter was employed would be considerably smaller than with conventional techniques.

For both catheters and other non-thrombogenic devices which can be made incorporating the present invention, the anticoagulant solution can, if desired, be replaced while the device is still in use. With the composite non-thrombogenic materials proposed in the prior art, such replacement would involve replacement of the whole material or the device from which it was formed.

Because the devices of the invention are made from relatively thin, light-weight materials, they can be used in applications where thicker, heavier materials would be inappropriate. In particular, the power requirement to drive the pump which provides the beating action for a cardiac assist device using the present invention will be far less than that for a bladder of polyurethane or other elastomer.

From the foregoing it will be also appreciated that non-thrombogenic surfaces constructed in accordance with the invention will find a multitude of other applications in the field of medical and veterinary science.

I claim:

1. A catheter including a reservoir having in use at least one bio-compatible non-thrombogenic surface; said reservoir being defined by flexible spaced apart walls at least one of which is a bio-compatible polymeric material through which anticoagulant solution contained in use by said reservoir may permeate thus providing a predetermined and controlled diffusion rate of anticoagulant solution, wherein said reservoir is formed from a collapsible flexible tube of said bio-compatible polymeric material having a hollow wall consisting of an inner wall defining a central lumen and an outer wall separable from the inner wall so as to define a substantially annular interwall passageway, the inner and outer walls fully enclosing the interwall passageway along an entire length of the catheter to form said reservoir.

2. A catheter as claimed in claim 1, wherein injection means are operatively associated with said hollow wall tube and whereby anticoagulant solution may be injected into and maintained under pressure in said interwall passageway.

3. A catheter as claimed in claim 1, wherein the inner and outer walls of the hollow wall tube merge at one end of said tube and are sealed at their free ends to at least one sealing member thereby enclosing said interwall passageway.

4. A catheter as claimed in claim 2, wherein the inner and outer walls of the hollow wall tube merge at one end of said tube and are sealed at their free ends to at least one sealing member thereby enclosing said interwall passageway.

5. A catheter as claimed in claim 1, wherein said bio-compatible polymeric material is formed as a continuous surface of said reservoir.

6. A cardiac assist device comprising:
a reservoir having in use at least one continuous bio-compatible non-thrombogenic surface;
said reservoir being defined by flexible spaced apart walls at least one of which is a bio-compatible polymeric material through which anticoagulant solution contained in use by said reservoir may permeate thus providing a predetermined and controlled diffusion rate of anticoagulant solution and wherein said reservoir is defined between an inner wall of a continuous surface of flexible gas tight material forming a bladder and an outer wall of said bio-compatible polymeric material spaced apart from said inner wall so as to define a substantially annular interwall passageway, the inner and outer walls fully enclosing the interwall passageway along an entire length of the cardiac assist device;
said inner and outer walls merging with an integral hollow walled entry tube to the interior of the bladder;
means for introducing anticoagulant solution into said reservoir; and
means for controlled inflation and deflation of said bladder which is continually inflated and deflated in use.

7. A cardiac assist device as claimed in claim 6, wherein a collar of permeable material defines, with the outer wall of the assist device entry tube, an annular chamber into which antibacterial solution can be injected, said annular chamber being located in use where the entry tube passes through skin and tissue.

* * * * *